United States Patent [19]

Brown

[11] 4,239,631
[45] Dec. 16, 1980

[54] CATIONIC SURFACTANT COMPOSITIONS COMPATIBLE WITH ANIONIC SURFACTANTS

[75] Inventor: Herman Brown, Teaneck, N.J.

[73] Assignee: Finetex Incorporated, Elmwood Park, N.J.

[21] Appl. No.: 102,555

[22] Filed: Dec. 11, 1979

Related U.S. Application Data

[63] Continuation-in-part of Ser. No. 17,186, Mar. 5, 1979, abandoned.

[51] Int. Cl.$^3$ .......................... C11D 1/4; C11D 1/62; D06M 0/00
[52] U.S. Cl. ................................. 252/8.75; 252/8.8; 252/545; 252/547; 252/548; 252/DIG. 13; 252/DIG. 14; 260/401; 260/404.5
[58] Field of Search ................ 252/8.75, 8.8, 545, 252/547, 548, DIG. 14; 260/501.15, 402.5, 404.5 Q, 404.5 N, 567.6 M; 424/70; 260/561 S, 401

[56] References Cited

U.S. PATENT DOCUMENTS

| | | | |
|---|---|---|---|
| 2,551,392 | 5/1951 | Pikl | 260/404.5 |
| 2,927,126 | 3/1960 | Pursglove | 260/404.5 C N |
| 2,928,831 | 3/1960 | Surrey | 260/247.5 |
| 3,247,215 | 4/1966 | Fisher et al. | 260/294.9 |
| 3,401,119 | 9/1968 | Froehlich | 252/117 |
| 3,492,324 | 1/1970 | Blackman | 260/404.5 |
| 3,833,597 | 9/1974 | Hardy et al. | 260/295 Q |
| 3,933,871 | 1/1976 | Armstrong | 260/401 |
| 3,959,461 | 5/1976 | Bailey et al. | 424/70 |
| 4,102,795 | 7/1978 | Minegishi et al. | 252/8.9 |
| 4,110,358 | 8/1978 | Braunwarth | 260/404.5 Q |

*Primary Examiner*—P. E. Willis, Jr.
*Attorney, Agent, or Firm*—Weingram & Klauber

[57] ABSTRACT

A cationic surfactant composition is disclosed which is compatible with anionic surfactants, and which when added thereto provides a system for use in simultaneous cleansing and conditioning of hair, textiles and the like. The cationic surfactant composition comprises a mixture of the diethyl sulfate salts of the cyanoethylated fatty acid amides

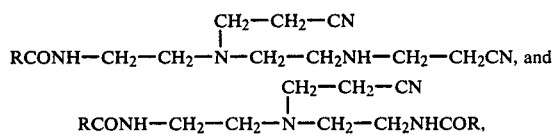

where R is an unbranched hydrocarbon chain including from 17 to 21 carbon atoms.

14 Claims, No Drawings

CATIONIC SURFACTANT COMPOSITIONS COMPATIBLE WITH ANIONIC SURFACTANTS

BACKGROUND OF INVENTION

This application is a continuation-in-part of my co-pending application, Ser. No. 17,186, filed Mar. 5, 1979, now abandoned.

This invention relates generally to chemical compositions useful in the cleansing of human hair, and in the cleansing of various fibrous materials such as textiles and the like; and more specifically relates to an improved surfactant system, wherein a cationic surfactant composition is combined with anionic surfactants to provide an improved surfactant system which simultaneously cleanses and conditions the materials being thereby treated.

Various cationic surfactants have long been known to be extremely useful agents for treating human hair and various fibrous textile materials and the like, in order to soften the thereby treated materials, and in other respects condition the said materials to improve certain qualities thereof. Thus in the toiletry field, such cationic materials as stearyl dimethyl benzyl ammonium chloride have long been utilized in the treatment of hair—the procedure normally being to employ the cationic agent subsequent to shampooing, in order to detangle and condition the hair. So called "fly-away" is also reduced by application of these agents, because of their antistatic properties.

A closely related use of the aforementioned cationic surfactants occurs where textiles are cleansed by use of anionic detergents. In particular, a suitable cationic composition is often employed following the cleansing treatment by the detergent. Thus for example, such procedure is used in normal laundering, where a fabric softener constituting a cationic agent is added during the final rinsing stage. Similar procedures are used in other cleansing operations, e.g. in shampooing of carpeting or rugs. In all these instances, as a result of use of the cationic agents, the material, be it textile, carpeting or the like, is softened, its general appearance improved, antistatic properties are lent to the material, etc., all as is well-known in the present art.

Over the course of many years, efforts have been made to combine a cationic surfactant composition of the type discussed above, with an anionic detergent composition, in order to provide in a single system, the capability for both cleansing and conditioning. But by and large, such efforts have met with only limited success.

Thus it has been known that by careful selection of the anionic and cationic compositions, and especially by selection of critically correct proportions, one can avoid the production of the precipitates which are the general rule where the differing compositions are intermixed. But as indicated, the proportions must be very accurately regulated in order to enable production of the complexes which have appeared to be critical to prevent precipitate formation. Similarly, even where so produced, such prior art combined cationic and anionic systems, have tended to have quite limited shelf-life, or have displayed other objectionable characteristics such as unacceptable irritation to the eyes and/or skin.

In accordance with the foregoing, it may be regarded as an object of the present invention, to provide a cationic surfactant composition which is compatible with anionic surfactants, and which when added thereto provides a system for use in simultaneous cleansing and conditioning of hair, textiles and the like.

It is a further object of the present invention, to provide a surfactant system containing both an anionic and a cationic surfactant, which leads the resultant system the capability of use in simultaneous cleansing and conditioning of human hair, and of textiles, fabrics and the like.

It is an additional object of the invention to provide an improved chemical system of the foregoing character, wherein the cationic surfactant composition may be added in virtually any proportions to the anionic surfactant composition, without producing undesired precipitates, and wherein the resultant surfactant system has high stability and long shelf-life.

SUMMARY OF INVENTION

Now in accordance with the present invention, the foregoing objects, and others as will become apparent in the course of the instant specification, are achieved by use of a cationic surfactant composition which is compatible with anionic surfactants, and which when added thereto provides a system useful in simultaneous cleansing and conditioning of human hair, of fabrics, textiles or the like. The cationic surfactant composition comprises a mixture of the diethyl sulfate salts of the cyanoethylated fatty acid amides

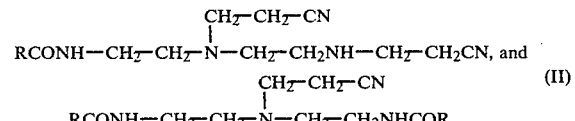

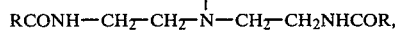

where R is an unbranched hydrocarbon chain of from 17 to 21 carbon atoms. The corresponding diethyl sulfate salts of these two bases are as follows:

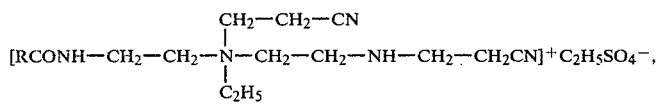

and

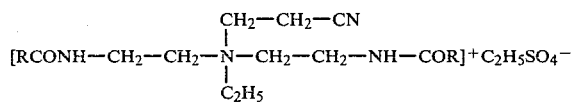

The salts III and IV are preferably present in the mixture in the ratio by mole percent of the active ingredients of the mixture, of from about 1:2 to about 1:3. Where, e.g. R=17, the said cationic composition comprises a mixture of the diethyl sulfate salts of the two following cyanoethylated stearamides:

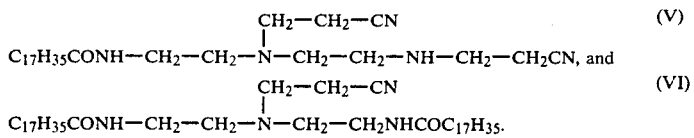

(V), (VI)

The corresponding diethyl sulfate salts of these two bases are as follows:

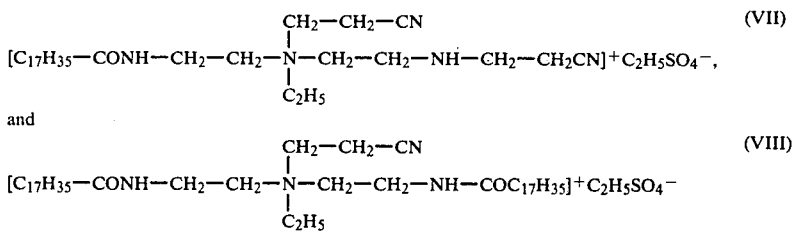

(VII), (VIII)

Similarly, where R=21, the said cationic composition is a mixture of the cyanoethylated behenamides:

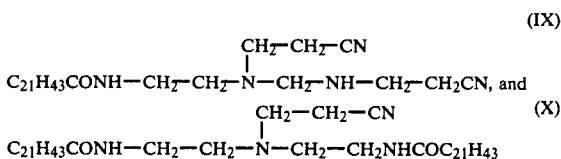

(IX), (X)

The corresponding diethyl sulfate salts of (IX) and (X) are as follows:

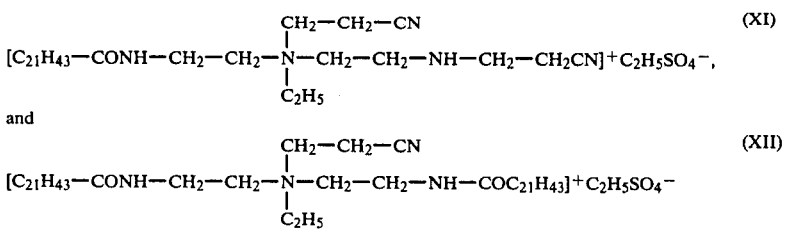

(XI), (XII)

In preparing the diethyl sulfate salts (III) and (IV), it is preferable to avoid utilizing an excess of diethyl sulfate. The latter compound has in some instances been found to irritate the skin, and if used in excess, unreacted diethyl sulfate can remain in the resultant composition. Preferably therefore, the cationic surfactant compositions of the present invention will comprise by weight from 50 to 99% of the aforementioned mixture of salts (III) and (IV), with the balance being a mixture of the corresponding (unreacted) cyanoethylated fatty acid amides (I) and (II).

The improved cleansing and conditioning surfactant systems of the invention, may comprise an aqueous solution of an anionic surfactant, together with from about 0.1 to 10% by weight of the aforementioned cationic surfactant composition. In accordance with a further aspect of the present invention, it has been found that the inclusion of from about 2 to 5% by weight of a lauric diethanolamide in the cleansing and conditioning formulations of the invention, improves shelf-life stability. It has also been found that if the anionic is a taurate, such as sodium N-methyl-N cocoyl taurate or N-methyl-N-oleoyl taurate, the systems are yet further stabilized to produce still better shelf life.

The improved cleansing and conditioning systems are prepared by mixing an aqueous solution of one or more of the anionic surfactants with the desired proportion of the cationic composition. The anionic surfactants can include such compounds as lauryl sulfates, lauryl ether sulfates, alkyl benzene sulfonates, sulfosuccinates, phosphate esters, and taurates. Direct additions of the cationic composition may be made at virtually all normal use aqueous concentrations. Depending upon the specifically contemplated use and purposes of the resulting cleansing and condition system, additional agents may also be added during this admixture, such as foam stabilizers, the aforementioned lauric diethanolamide (lauric DEA) or so forth.

DESCRIPTION OF PREFERRED EMBODIMENT

Practice of the present invention is illustrated by the following examples.

EXAMPLES 1 THROUGH 3

In these Examples, three differing conditioning shampoo systems in accordance with the invention, were prepared. The proportions of the components in the three systems (Ex. 1, Ex. 2, and Ex. 3) are set forth in Table I below:

TABLE I

Conditioning Shampoos

| Component | % Actives by Weight | | |
|---|---|---|---|
| | Ex. 1 | Ex. 2 | Ex. 3 |
| sodium lauryl ether (2) sulfate* | 15.0 | 15.0 | 6.0 |
| sodium N-methyl-N-oleoyl taurate** | — | — | 16.5 |
| lauric diethanolamide (DEA)*** | 3.0 | 3.0 | 2.0 |
| mixture of salts XI and XII with corresponding fatty acid amides# (17% actives) | — | 1.2 | — |
| mixture of sales VII and VIII with corresponding fatty acid amides## (14% actives) | 2.0 | — | 1.5 |
| water | bal. | bal. | bal. |

TABLE I-continued

| | Conditioning Shampoos | | |
|---|---|---|---|
| | | % Actives by Weight | |
| Component | Ex. 1 | Ex. 2 | Ex. 3 |
| pH | 7.52 | 8.1 | 7.58 |

*STANDAPOL ES-2 product of Henkel, Inc., Hoboken, N.J. used as a 28% actives composition.
**TAURANOL MS product of Finetex, Inc., used as a 33% actives composition.
***AMINOL LM-5C product of Finetex, Inc., used as 100% actives composition.
Mixture included by mole percent of active ingredient: 20.5 salt XI, 41.5 salt XII, 12.5 fatty amide IX, and 25.5 fatty amide X. This is an approximate ratio by mole percent of 1:2 for the respective salts and for the respective corresponding amides.
Mixture included by mole percent of active ingredient: 15.2 salt VII, 45.7 salt VIII, 9.8 fatty amide V, 29.3 fatty amide VI. This is an approximate ratio by mole percent of 1:3 for the respective salts and for the respective corresponding amides.

Each of the new systems 1, 2 and 3, following preparation was used for shampooing and conditioning human hair by customary procedures. The hair thus treated, was found to have good body, and displayed smooth, soft lubricating qualities against the hand. The hair also exhibited very little fly-away i.e. antistatic properties were good, and the ability to comb same was regarded as excellent. In each instance, the mentioned qualities were directly compared to results yielded utilizing a similar treatment by the anionic detergent alone, i.e. without modification by the cationic agents shown in Table I.

It may also be pointed out that by incorporation of anionics such as the taurates specified in Table I, shelflife stability of systems produced in accordance with the invention, are found to be particularly impressive. For example, in a formulation of the type set forth in Table I, a study of stability after four months, indicated no deterioration whatsoever in the said systems.

EXAMPLE 4

In this Example, a system in accordance with the invention was prepared, which was intended for and was used in rug shampooing. The components of the composition are as set forth in Table II below:

TABLE II

| Rug Shampoo | |
|---|---|
| Component | % Actives by Weight |
| sodium lauryl sulfate* | 20.0 |
| dimethyl cocoamine oxide** | 3.0 |
| mixture of sales VII and VIII with corresponding fatty acid amides## (14% actives) | 2.0 |
| water | bal. |

*AVIROL 101 SPECIAL product of Henkel, Inc., Hoboken, N.J. used as a 30% actives composition.
**AROMOX DMC product of Ashland Chemical, Columbus, Ohio, employed here as a foam stabilizer, and used as a 40% actives composition.
Mixture included by mole percent of active ingredient: 15.2 salt VII, 45.7 salt VIII, 9.8 fatty amide V, 29.3 fatty amide VI. This is an approximate ratio by mole percent of 1:3 for the respective salts and for the respective corresponding amides.

When the system of Table II was utilized in the shampooing of a rug, the resultant cleaned and conditioned rug displayed excellent softness, and good antistatic properties. It should be noted that while the water content of the compositions in the Examples thus far set forth, has been appropriate to reflect the percentage actives indicated, the compositions can also in most instances, be further diluted without detrimental effect.

EXAMPLES 5 THROUGH 7

In the formulation of these Examples, chemical systems in accordance with the invention were prepared by modification of liquid laundry detergents. More specifically, three liquid laundry detergent systems containing a cationic composition pursuant to the invention were prepared, having proportions of components as identified in Table III below:

TABLE III

| Liquid Laundry Detergents Containing a Cationic | | | |
|---|---|---|---|
| | % of Actives by Weight | | |
| Component | Ex. 5 | Ex. 6 | Ex. 7 |
| TEA dodecyl benzene sulfonate* | 28.5 | — | — |
| sodium dodecyl benzene sulfonate** | — | 13.7 | — |
| $CH_3(CH_2)_{11-14}$ (O—$CH_2$—$CH_2)_9$OH*** | — | 20.0 | 35.0 |
| sodium lauryl ether (2) sulfate | — | — | 2.8 |
| lauric DEA | 3.0 | — | — |
| TEA | — | 5.0 | 5.0 |
| KCl | — | — | 1.0 |
| mixture of salts VII and VIII with corresponding fatty acid amides## (14% actives) | 5.0 | 6.0 | — |
| mixture of sales VII and VIII with corresponding fatty acid amides## (92% actives) | — | — | 9.2 |
| ethanol | — | — | 12.6 |
| water | bal. | bal. | bal. |
| pH | 7.4 | 9.1 | 8.3 |

*RUETERG 60T product of Finetex, Inc., used as a 60% actives composition.
**SULFRAMIN 90 Flake product of Witco Chemical Co., N.J., used as a 91% actives composition.
***NEODOL 25-9 product of Shell Chemical Co./Industrial Chemicals Division, N.Y., N.Y. This is a 9 mole ethoxylate of $C_{12}$, $C_{13}$, $C_{14}$ and $C_{15}$ linear primary alcohols.
STANDAPOL ES-2 product of Henkel, Inc., used as a 28% actives composition.
AMINOL LM-5C product of Finetex, Inc., employed here as a foam stabilizer and booster, and used as a 100% actives composition.
Mixture included by mole percent of active ingredient: 15.2 salt VII, 45.7 salt VIII, 9.8 fatty amide V, 29.3 fatty amide VI. This is an approximate ratio by mole percent of 1:3 for the respective salts and for the respective corresponding amides.

In each instance, the resultant improved detergent systems of Examples 5 through 7 were utilized in the washing of various fabrics of conventional methods. It was found that the combined system of the invention, effectively prevented residual harshness in the fabrics, which fabrics subsequent to treatment were of excellent soft quality to the touch.

EXAMPLE 8

In this example, a chemical system in accordance with the invention was prepared, which was a modified liquid cold water dainty fabric detergent system. The formulation is set forth in Table IV below:

TABLE IV

| Liquid Cold Water Dainty Fabric Detergent | |
|---|---|
| Component | % Actives by Weight |
| sodium lauryl ether (2) sulfate* | 15.9 |
| lauric DEA** | 5.0 |
| mixture of salts VII and VIII with corresponding fatty acid amides## (14% actives) | 5.0 |
| water | bal. |
| pH | 7.4 |

*STANDAPOL ES-2 product of Henkel, Inc., used a 28% actives composition.
**AMINOL LM-5C product of Finetex, Inc., used as a 100% actives composition.
Mixture included by mole percent of active ingredient: 15.2 salt VII, 45.7 salt VIII, 9.8 fatty amide V, 29.3 fatty amide VI. This is an approximate ratio by mole percent of 1:3 for the respective salts and for the respective corresponding amides.

The improved detergent system of this Example was utilized in the washing of various delicate fabrics by conventional methods. The resulting fabrics were found to be well-cleansed, residual harshness was absent, the fabrics were soft to the touch, and had good anti-static qualities.

While the present invention has been particularly set forth in terms of specific embodiments thereof, it will be understood in view of the instant disclosure, that numerous variations upon the invention are now enable to those skilled in the art, which variations yet reside within the scope of the present teaching. Accordingly, the invention is to be broadly construed, and limited only by the scope and spirit of the claims now appended hereto.

I claim:

1. A cationic surfactant composition which is compatible with anionic surfactants, and which in aqueous admixture therewith provides a system useful in simultaneous cleansing and conditioning of hair, fabrics, textiles and the like; said composition comprising:

a mixture of the diethyl sulfate salts of the cyanoethylated fatty acid amides

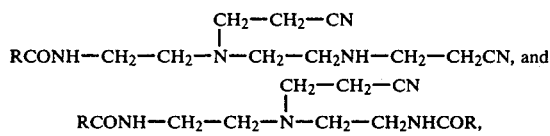

where R is an unbranched hydrocarbon chain, having from 17 to 21 carbon atoms, and said salts being in the respective ratio by mole percent of the active ingredients of said mixture of from about 1:2 to about 1:3.

2. A composition in accordance with claim 1, wherein R has 17 carbon atoms.

3. A composition in accordance with claim 1, wherein R has 21 carbon atoms.

4. A composition in accordance with claim 1, further including unreacted quantities of the said fatty acid amides corresponding to said salts, said salts comprising from 50 to 99% by weight of the said composition, with the balance being said corresponding fatty acid amides, the ratio by mole percent between said amides being approximately that of the said corresponding salts.

5. A surfactant system for use in simultaneous cleansing and conditioning of hair, fabrics, textiles and the like, comprising an aqueous solution of an anionic surfactant, and from about 0.1 to 10% by weight of a cationic surfactant composition comprising a mixture of the diethyl sulfate salts of the cyanoethylated fatty acid amides

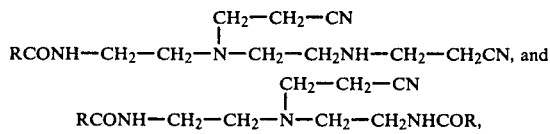

where R is an unbranched hydrocarbon chain, having from 17 to 21 carbon atoms, and said salts being in the respective ratio by mole percent of the active ingredients of said mixture of from about 1:2 to about 1:3.

6. A surfactant system in accordance with claim 5, wherein R has 17 carbon atoms.

7. A surfactant system in accordance with claim 5, wherein R has 21 carbon atoms.

8. A surfactant system in accordance with claim 5, wherein said cationic composition further includes unreacted quantities of the said fatty acid amides corresponding to said salts, said salts comprising from 50 to 99% by weight of the said cationic composition, with the balance thereof, being said corresponding fatty acid amides, the ratio by mole percent between said amides being approximately that of the said corresponding salts.

9. A surfactant system in accordance with claim 5, wherein said anionic surfactant is a taurate.

10. A surfactant system in accordance with claim 5, further including from about 2 to 5% by weight of a lauric diethanolamide.

11. A cationic surfactant composition which is compatible with anionic surfactants, and which in aqueous admixture therewith provides a system useful in simultaneous cleansing and conditioning of hair, fabrics, textiles and the like; said composition comprising: a mixture of the diethyl sulfate salts:

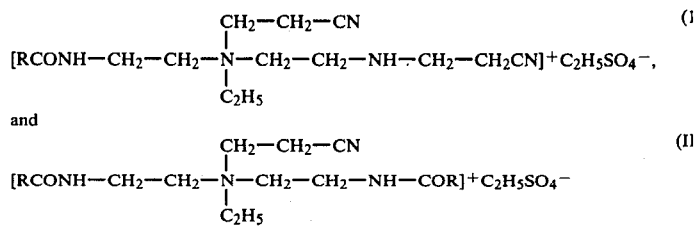

where R is an unbranched hydrocarbon chain having from 17 to 21 carbon atoms, and said salts (1) and (2) being in the respective ratio by mole percent of the active ingredients of said mixture of from about 1:2 to about 1:3.

12. A composition in accordance with claim 11, wherein R has 17 carbon atoms, and wherein the ratio between salt (1) and (2) is about 1:3.

13. A composition in accordance with claim 1, wherein R has 21 carbon atoms, and wherein the ratio between salt (1) and (2) is about 1:2.

14. A composition in accordance with claim 11, further including unreacted quantities of the fatty acid amides

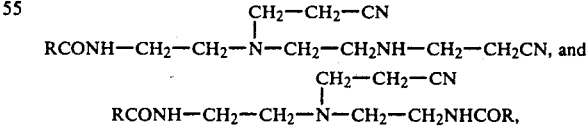

corresponding to said salts, said salts comprising from 50 to 99% by weight of the said composition, with the balance being said corresponding fatty acid amides.

* * * * *